(12) United States Patent
Kleimola et al.

(10) Patent No.: US 7,544,504 B2
(45) Date of Patent: *Jun. 9, 2009

(54) DIAGNOSTIC METHODS

(75) Inventors: Vesa Kleimola, Turku (FI); Erkki Eerola, Turku (FI); Markku Viander, Turku (FI)

(73) Assignee: Bionavis Ltd., Tampere (FI)

( * ) Notice: Subject to any disclaimer, the term of this patent is extended or adjusted under 35 U.S.C. 154(b) by 0 days.

This patent is subject to a terminal disclaimer.

(21) Appl. No.: 10/164,555

(22) Filed: Jun. 10, 2002

(65) Prior Publication Data

US 2003/0124632 A1   Jul. 3, 2003

(30) Foreign Application Priority Data

Dec. 31, 2001   (FI)   ................................... 20012603

(51) Int. Cl.
C12M 1/34   (2006.01)

(52) U.S. Cl. .................. 435/287.2; 435/288.7; 435/808; 435/287.9; 436/527; 436/805; 436/806; 422/57; 422/82.05; 422/82.11; 385/129; 385/130

(58) Field of Classification Search ................. 422/427, 422/422, 423, 489, 501, 491, 492, 496, 497, 422/500, 56, 57, 58, 60, 947, 55; 351/160 H, 351/160 R; 435/7.9, 7.92, 7.1, 6, 7.32, 4, 435/7.4, 7.93, 7.94, 287.1, 287.2, 7.95, 805, 435/810, 969, 970, 1.73; 436/169, 170, 518, 436/531, 524, 527, 805, 810, 525, 514; 525/100; 424/1.73, 9.35
See application file for complete search history.

(56) References Cited

U.S. PATENT DOCUMENTS

| 4,775,637 | A | | 10/1988 | Sutherland et al. |
| 4,931,384 | A | * | 6/1990 | Layton et al. ............... 435/7.31 |
| 5,135,876 | A | | 8/1992 | Andrade et al. |
| 5,242,828 | A | | 9/1993 | Johnsson et al. |
| 5,262,156 | A | | 11/1993 | Alemohammad |

(Continued)

FOREIGN PATENT DOCUMENTS

CN   1303013   7/2001

(Continued)

OTHER PUBLICATIONS

Disley, Darren M et al, Biosensors and Bioelectronics, vol. 13(3-4), pp. 383-396, 1998.*

(Continued)

*Primary Examiner*—Robert B Mondesi
*Assistant Examiner*—Ginny Portner
(74) *Attorney, Agent, or Firm*—Buchanan Ingersoll & Rooney PC

(57) ABSTRACT

The present invention relates to novel methods for the diagnosis of *Helicobacter pylori* infection. Specifically, the present invention relates to novel non-invasive methods for the detection of the presence or absence of a *Helicobacter pylori* antigen or a metabolite produced by the bacterium in a biological sample with a biosensor-based measurement. The present invention also related to the use of a biosensor containing specific antibodies against *H. pylori* or antigen-binding fragments thereof immobilized thereto together with biomolecule-repellent polymers preventing the non-specific binding. The invention also relates to test kits useful in the methods.

16 Claims, 3 Drawing Sheets

U.S. PATENT DOCUMENTS

| | | | |
|---|---|---|---|
| 5,322,798 | A | 6/1994 | Sadowski |
| 5,369,007 | A * | 11/1994 | Kidwell ............... 435/7.9 |
| 5,492,840 | A * | 2/1996 | Malmqvist et al. ......... 436/518 |
| 5,677,196 | A | 10/1997 | Herron et al. |
| 5,788,687 | A * | 8/1998 | Batich et al. ............ 604/890.1 |
| 5,871,942 | A | 2/1999 | Kozak et al. |
| 5,919,712 | A * | 7/1999 | Herron et al. ............. 436/518 |
| 5,932,430 | A | 8/1999 | Kozak et al. |
| 6,039,959 | A * | 3/2000 | Burnie .................. 424/234.1 |
| 6,048,735 | A * | 4/2000 | Hessel et al. ............. 436/518 |
| 6,068,985 | A | 5/2000 | Clancy et al. |
| 6,153,390 | A * | 11/2000 | Cover et al. .................. 435/6 |
| 6,245,574 | B1 * | 6/2001 | Waldner et al. ............. 436/79 |
| 6,322,963 | B1 * | 11/2001 | Bauer ......................... 435/4 |
| 6,413,784 | B1 * | 7/2002 | Lundsgaard et al. ........ 436/518 |
| 6,503,701 | B1 * | 1/2003 | Bauer ......................... 435/4 |
| 6,753,190 | B1 * | 6/2004 | Okada et al. .............. 436/518 |
| 6,770,488 | B1 * | 8/2004 | Carron et al. ............. 436/525 |
| 6,833,267 | B1 * | 12/2004 | Kayyem ................ 435/287.1 |
| 6,844,028 | B2 | 1/2005 | Mao et al. |
| 6,849,414 | B2 * | 2/2005 | Guan et al. ................. 435/7.1 |
| 7,052,854 | B2 * | 5/2006 | Melker et al. .............. 435/7.1 |
| 7,332,327 | B2 * | 2/2008 | Vikholm et al. ......... 435/287.2 |
| 2002/0005953 | A1 * | 1/2002 | Negami et al. .............. 356/445 |
| 2002/0090660 | A1 * | 7/2002 | Yi et al. ..................... 435/7.32 |
| 2002/0102405 | A1 | 8/2002 | Chapman et al. |
| 2002/0127623 | A1 * | 9/2002 | Minshull et al. ........... 435/7.92 |
| 2002/0197659 | A1 * | 12/2002 | Knuth et al. .............. 435/7.23 |
| 2003/0004426 | A1 * | 1/2003 | Melker et al. .............. 600/532 |
| 2003/0059954 | A1 * | 3/2003 | Vikholm et al. ............ 436/518 |
| 2003/0103901 | A1 * | 6/2003 | Leyland-Jones ............ 424/9.2 |
| 2003/0124632 | A1 * | 7/2003 | Kleimola et al. ........... 435/7.32 |
| 2003/0124633 | A1 * | 7/2003 | Kleimola et al. ........... 435/7.32 |
| 2003/0219424 | A1 * | 11/2003 | Nalan ...................... 424/93.21 |
| 2004/0023316 | A1 * | 2/2004 | Reiter et al. ............... 435/7.32 |
| 2004/0029259 | A1 * | 2/2004 | McDevitt et al. ......... 435/287.2 |
| 2004/0038307 | A1 * | 2/2004 | Lee et al. .................... 435/7.1 |
| 2004/0052729 | A1 * | 3/2004 | Penades et al. ............ 424/1.73 |
| 2004/0100376 | A1 * | 5/2004 | Lye et al. ............... 340/539.12 |
| 2004/0101826 | A1 * | 5/2004 | Jones et al. .................... 435/5 |
| 2004/0146899 | A1 * | 7/2004 | Kayyem ....................... 435/6 |
| 2004/0161804 | A1 * | 8/2004 | McCash et al. .............. 435/7.2 |
| 2004/0180380 | A1 * | 9/2004 | Lee et al. ..................... 435/7.1 |
| 2004/0241883 | A1 * | 12/2004 | Tanga et al. ................ 436/525 |
| 2004/0253624 | A1 * | 12/2004 | Smith et al. .................... 435/6 |
| 2005/0069911 | A1 * | 3/2005 | Lee et al. ........................ 435/6 |
| 2005/0095601 | A1 * | 5/2005 | Cullum et al. .................. 435/6 |
| 2005/0101841 | A9 * | 5/2005 | Kaylor et al. ............... 600/300 |
| 2006/0035270 | A1 * | 2/2006 | Lee et al. ........................ 435/6 |
| 2006/0057707 | A1 * | 3/2006 | Cunningham et al. .... 435/287.1 |
| 2008/0145441 | A1 * | 6/2008 | Penades et al. .............. 424/499 |

FOREIGN PATENT DOCUMENTS

| | | |
|---|---|---|
| DE | 19806642 A1 | 8/1999 |
| DE | 10002895 | 7/2001 |
| EP | 0485874 | 5/1992 |
| EP | 0645015 B1 * | 3/1995 |
| EP | 0806667 B1 | 11/1997 |
| WO | 98/24885 | 6/1998 |
| WO | 00/26671 * | 3/2000 |
| WO | 00/26671 A1 | 5/2000 |
| WO | 00/32091 * | 6/2000 |
| WO | 00/57182 * | 9/2000 |
| WO | 00/56352 A1 | 11/2000 |
| WO | 00/77522 * | 12/2000 |
| WO | 01/27612 A2 | 4/2001 |
| WO | 01/27613 A2 | 4/2001 |
| WO | 01/40801 | 6/2001 |
| WO | 0144815 | 6/2001 |
| WO | 03/056338 * | 7/2003 |

OTHER PUBLICATIONS

Houimel, M et al, Tumor biology, the journal of the International Society for Oncodevelopmental Biology and Medicine,(Switzerland) Jan.-Feb. 2001, Voo. 22(1), pp. 36-44 (abstract only).*

Nishimura, T et al, Electrochemistry, vol. 68, pp. 916-919, 2000.*

Tomb, JF et al, Nature, vol. 388, Aug. 7, 1997,pp. 539-547, The complete genome sequence of the gastric pathogen *Helicobacter pylori*.*

Utt, M et al, FEMS immunology and medical microbiology (Netherlands) Mar. 2001, vol. 30(2), pp. 109-113.*

Nishimura, T et al, Electrochemistry, vol. 68, 2000, pp. 916-919.*

Utt et al (2001), FEMS Immunology and Medical Microbiology, vol. 30, pp. 109-113, *Helicobacter pylori* vacuolating cytotoxin binding to a putative cell surface receptor, heparin sulfate, studied by surface plasmon resonance.*

Houimel, M et al, Tumor Biology, vol. 22, pp. 36-44, 2001, Selection of Human single chain Fv antibody fragments binding and hibiting *Helicobacter pylori* urease.*

Tumor Biology, vol. 22(1), 2001, Selection of Human singl chain Fv antibody fragments binding and inhibiting *Helicbacter pylori* urease, Houimel et al, (abstract only).*

Nishimura, Tomoaki et al, Electrochemistry, vol. 68, pp. 916-919, Measurement of *Helicobacter pylori* using anti its urease monoconal antibody by surface plasmon resonance.*

Nishimura et al, reference of record.*

R. Kellner et al. (Editors), "Analytical Chemistry" 1998, pp. 399-400, Wiley-VCH Verlag GmbH, Weinheim, Germany.

Tomoaki Nishimura, et al, "Measurement of *Helicobacter pylori* Using Anti Its Urease Monoclonal Antibody by Surface Plasmon Resonance," Electrochemistry, vol. 68, No. 11, pp. 916-919.

Darren M. Disley, et al, "Covalent coupling of immunoglobulin G to a poly(vinyl)alcohol-poly(acrylic acid) graft polymer as a method for fabricating the interfacial-recognition layer of a surface plasmon resonance immunosensor," Biensors & Bioelectronics, vol. 13, No. 3-4, pp. 383-396, 1998.

* cited by examiner

A

B

Fig. 4 Detection of *H. pylori* antigen in stool samples
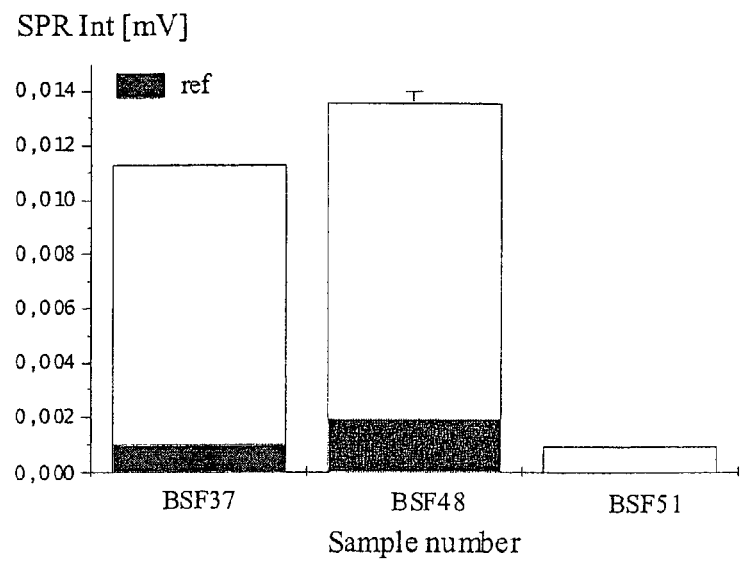
Fig. 5 Detection of *H. pylori* antigen in urine samples
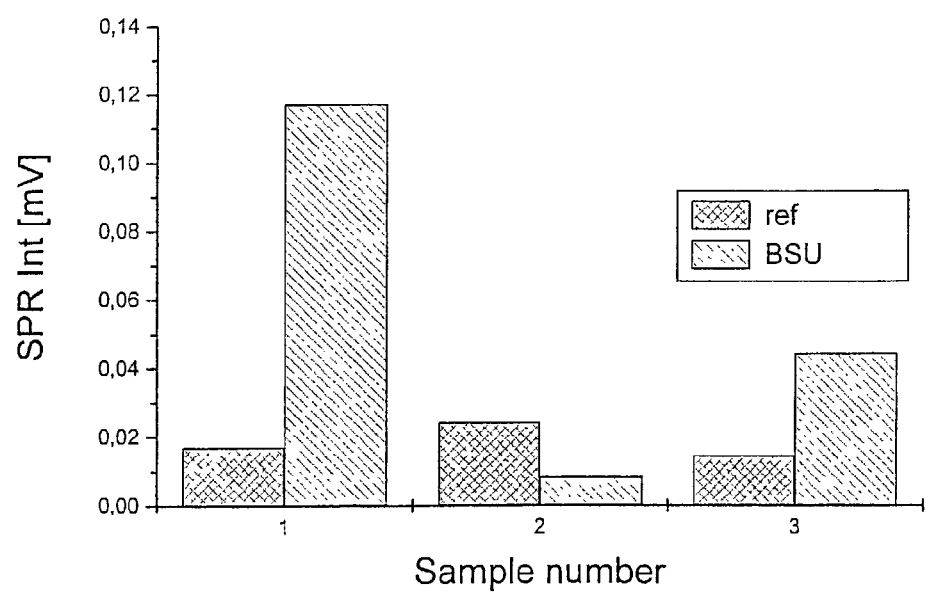

DIAGNOSTIC METHODS

FIELD OF THE INVENTION

The present invention relates to novel methods for the diagnosis of *Helicobacter pylori* infection. Specifically, the present invention relates to novel non-invasive methods for the detection of the presence or absence of a *Helicobacter pylori* antigen or a metabolite produced by the bacterium in a biological sample with a biosensor-based measurement. The present invention also related to the use of a biosensor containing specific antibodies against *H. pylori* or antigen-binding fragments thereof immobilized thereto together with biomolecule-repellent polymers preventing the non-specific binding. The invention also relates to test kits useful in the methods.

BACKGROUND OF THE INVENTION

*Helicobacter pylori* is a curved gram-negative bacterium found in the upper gastrointestinal tract of humans. Since the first isolation of the bacterium in 1982, a huge amount of evidence has accumulated on the association of *H. pylori* with various gastric disorders, including dyspepsia (heartburn, bloating and nausea), symptomatic or asymptomatic inflammation of gastric mucosa manifested as chronic superficial gastritis or chronic active gastritis, peptic ulcers of the stomach and duodenum, and even gastric cancer and various gastric lymphomas [Dunn, B. E., et al., Clinical Microbiology Reviews 10 (1997) 720-740]. At present, it is believed that nearly all cases of peptic ulcers formerly thought to be idiopathic are actually caused by *H. pylori* infection [NIH Consensus Conference, JAMA 276 (1994) 1710].

*H. pylori* is a world wide human pathogen. The other known species carrying the bacterium is nonhuman primates. *H. pylori* infections have been connected to the socio-economic development: in developing countries 70 to 90% of the population carries the bacterium, whereas in developed countries the prevalence of the infection is approximately 25 to 50%. The infection is acquired in childhood, usually before the age of 10 years, and is believed that the rate of the incidence decreases with improved hygiene. However, the route of transmittance of the infection is not definitely known, although faecal-oral and oral-oral routes are thought to be most important (Dunn, B. E., et al., supra).

Various methods and assays, both invasive and non-invasive, are available for the diagnosis of *H. pylori* infection. The invasive methods involve gastric or duodenal biopsies. The biopsy samples can be examined visually or histologically, cultured for the bacteria, tested for the urease enzyme produced by *H. pylori*, or analysed with gene technology. Commercial products are available for most of these methods. Non-invasive methods include serological tests for the detection of antibodies to *H. pylori* and urea breath test using $^{13}$C or $^{14}$C-labelled urea, for both of which multiple commercial tests are available. Additionally, assays measuring substrate metabolism of *H. pylori* in serum [Moulton-Barret, R. G., et al., Am. J. Gastroenterol 88 (1993) 369-374] and in urine [Pathak, C. M., et al., Am. J. Gastroenterol 89 (1993) 734-738] have been described.

Immunoassays measure the presence of IgG, IgA or IgM antibodies against *H. pylori* in patients' serum or blood samples (see, for example, U.S. Pat. No. 5,262,156; Pyloriset EIA-A and EIA-G, Orion Diagnostica, Finland), urine samples (see, for example, U.S. Pat. No. 5,262,156), and saliva or other mucous secretion specimen (see, for example, U.S. Pat. No. 6,068,985; Home Helicobacter Test, Ani Biotech Oy, Finland). The determination of antibodies against *H. pylori* suffer from several drawbacks, such as the strong dependence of the antigen preparation which is used to capture the antibodies, cross reactions of antibodies from related bacterial species, and the relatively long time needed for reliable test results. The accuracy of the so-called "office-based" or "near-patient" tests offered for use in doctor's offices is poorer than that of conventional laboratory assays. [Cohen, H., et al., Gastroenterology 110 (1996) A83; Sadowski, D., et al., Gastroenterology 110 (1996) A246]. Importantly, these assays relying on the detection of specific antibodies against *H. pylori* are less suitable for use in the evaluation and follow-up of the treatment and cure, since the elevated antibody levels maintain for a long period of time after the treatment and cure of the infection. Follow-up studies show great variation in the decline of the antibody levels after treatment [Kosunen, T. U., et al., Lancet 339 (1992) 893-895; Cutler, A., et al., Dig. Dis. Sci. 38 (1993) 2262-2266], but usually several months are needed for a decline, which reliably predicts the cure.

The detection of *H. pylori* antigens or metabolites instead of specific antibodies against *H. pylori* in a biological sample addresses this drawback. U.S. Pat. Nos. 5,716,791, 5,871,942 and 5,932,430 disclose, inter alia, methods for the detection of *H. pylori* antigens in faecal samples by complexing the antigen with a polyclonal antibody and detecting the complex thus formed by a second antibody. International patent application WO01/44815 discloses the detection of *H. pylori* antigens in a blood samples with, for instance, an ELISA method. These methods are suggested for the follow-up of the effect of the treatment of *H. pylori* infection.

However, the conventional immunoassays rely on a marker molecule such as a radioactive label, an enzyme label, a fluorescent label or chemiluminescent label, and are laborious and time-consuming, since several incubation, washing and separation steps are needed before the actual detection. Additionally, for a reliable performance, they require a skilled personnel and rather expensive apparatuses. The sample, especially a faecal sample, may also represent a problem. Many patients find the collection of one faecal sample, let alone the collection of several faecal samples necessary for the follow-up, unpleasant and not hygienic, and their compliance to the treatment may suffer. Similarly, the personnel may dislike the handling of the faecal specimen and the preparation of samples for such assays due to the inherent infection risk.

Further improved diagnostic methods for the diagnosis of *H. pylori* infections are obviously needed.

Accordingly, one object of the present invention is to provide highly sensitive and specific methods and means for the non-invasive detection and determination of *H. pylori* antigens and/or metabolites produced by the bacterium in a biological sample.

Another object of the present invention is to provide improved methods and means for a reliable follow-up of the effect of pharmacotherapy in combating *H. pylori* infection and for the ascertainment of the cure of the patient with minor inconvenience to the patient.

A further object of the present invention is to provide improved methods and means for the detection of *H. pylori* infection, the methods being reliably applicable to the use in doctor's offices and in heath care centres, where the technical skills and routine of personnel may not be as advanced as in clinical laboratories.

A further object of the present invention is to provide improved methods and means for the detection of *H. pylori* infection, the methods being simple, rapid and real-timed so that the test results can be obtained even during the patient's visit at the hospital or the doctor's office, whereby several patient calls can be avoided.

SUMMARY OF THE INVENTION

It was unexpectedly found that it is possible to non-invasively detect the presence or the absence of *Helicobacter pylori* in a biological sample employing methods based on the use of a highly specific and sensitive biosensor and thereby meet the objects of the present invention. The biosensor useful in the present invention comprises a carrier substrate, onto which specific antibodies against *H. pylori* or antigen-binding fragments thereof have been directly attached together with biomolecule-repellent molecules, which cover the surface between the immobilized antibodies or the antibody fragments. These biomolecule-repellent molecules efficiently prevent the undesired non-specific binding of the analyte and the contaminant (bio)molecules present in the biological sample and highly increase the sensitivity of the assay. The use of such a biosensor affords reliable detection of *H. pylori* antigens and/or metabolites produced by the bacterium in any biological specimen.

The present invention relates to a non-invasive method for the detection of the presence or absence of a *Helicobacter pylori* antigen or a metabolite produced by the bacterium in a biological sample comprising contacting a biological sample obtained from a patient suffering or suspected of suffering from *H. pylori* infection with a biosensor comprising a carrier substrate, onto which antibodies against *H. pylori* or antigen-binding fragments together with biomolecule-repellent molecules have been attached, and detecting the signal resulting from the formation of an anti body-antigen-complex.

The present invention further relates to the use of a biosensor comprising a carrier substrate, onto which specific antibodies against *H. pylori* or antigen-binding fragments thereof have been directly attached together with biomolecule-repellent molecules, which cover the surface between the immobilized antibodies or the antigen-binding fragments thereof, for the diagnosis of *Helicobacter pylori* infection.

The present invention also relates to a test kit for the detection of the presence or absence of a *Helicobacter pylori* antigen or a metabolite produced by the bacterium in a biological sample, the test kit containing a biosensor comprising a carrier substrate, onto which specific antibodies against *H. pylori* or antigen-binding fragments thereof have been directly attached together with biomolecule-repellent molecules, which cover the surface between the immobilized antibodies or the antibody fragments, together with reagents needed for the detection.

DESCRIPTION OF THE DRAWINGS

FIG. 4 shows SPR binding isotherms of the detection of *H. pylori* in stool samples. The bar indicates two measurements with separate films. BSF37 and BSF48 are samples obtained from patients positive for *Helicobacter pylori* and BSF51 is a sample obtained from a patient negative for *Helicobacter pylori*. "ref" indicates the blank.

FIG. 5 shows SPR binding isotherms of the detection of *H. pylori* in urine samples. Samples 1 and 3 are samples obtained from patients positive for *Helicobacter pylori* and sample 2 is a sample obtained from a patient negative for *Helicobacter pylori*. "ref" indicates the blank and BSU indicates patient urine sample.

DETAILED DESCRIPTION OF THE INVENTION

The present invention is based on the development of methods and means sensitive and specific enough to detect and/or measure low amounts of antibody-antigen-complexes formed in an immunological reaction between an immobilized antibody or antigen-binding fragment thereof, which are specific to a *H. pylori* bacterium, an antigen thereof and/or a metabolite produced by the bacterium, and a *H. pylori* derived antigen. With such methods and means the *H. pylori* antigens and/or metabolites produced by the bacterium can be detected in any biological sample obtainable non-invasively from patients suffering from *H. pylori* infection.

The terms "a *H. pylori* antigen" and "a *H. pylori* derived antigen" as used herein refer to a surface antigen or an antigen resulting from the breakdown or metabolism of *H. pylori* bacterium. The terms "an antigen-binding fragment" and "an antibody fragment" as used herein refer to (Fab')$_2$ or Fab' fragments of antibodies specific to *H. pylori* antigens.

In the method of the present invention advantage is taken of a special carrier substrate and a biosensor comprising such a carrier substrate. These carrier substrates and biosensors are generally disclosed in Finnish Application 20011877, which is incorporated herein by reference. Carrier substrates useful in the present invention contain specific antibodies raised against *H. pylori* bacterium or *H. pylori* antigens or antigen-binding fragments of these antibodies, the antibodies being attached on the carrier substrate. Additionally, the carrier substrates also contain biomolecule-repellent monomer/polymer molecules attached onto the same carrier substrate as the antibodies or antibody fragments to prevent the non-specific binding of the analytes and undesired contaminant (bio)molecules present in the biological sample.

Figure 1:
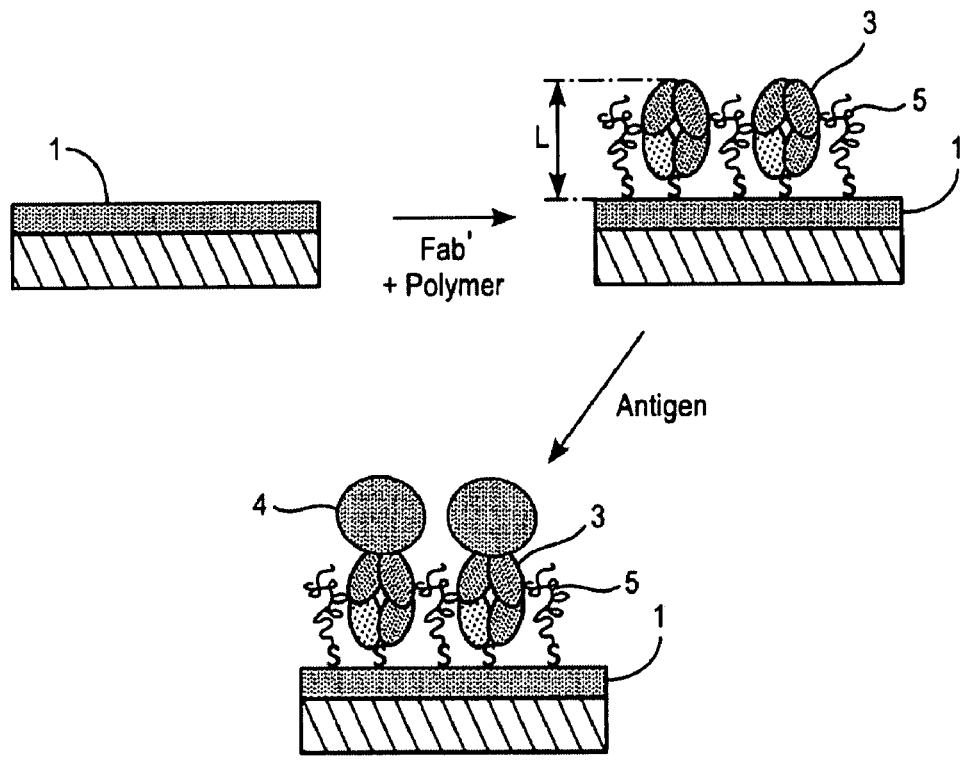
FIG. 1 is a schematic representation of a carrier substrate/biosensor used in the method of the present invention containing Fab' fragments of an antibody against *H. pylori* (3) together with biomolecule repellent-molecules (Polymer and 5) on the solid surface (1) of the carrier substrate/biosensor. Antigen (Antigen and 4) binds to the Fab' fragments. L denotes the length of the Fab' fragments.

Specifically, the substrate carries antibodies against *H. pylori* or their antigen-binding fragments immobilized, through a functional group present in the antibodies or antibody fragments, directly on a solid surface of the carrier substrate to form a layer of oriented antigen-binding sites (FIG. 1). The antibodies or antibody fragments become self-assembled on the surface of the substrate with the active antigen-binding site being exposed and the functional group having affinity to the substrate surface being bound to the surface.

Free sulphydryl groups in the antibodies or the antibody fragments serve as functional groups and can chemisorp on metal surfaces, such as gold, silver, copper, aluminium and palladium surfaces, through covalent bonds between the metal atoms and the sulphur atoms and thereby form a monolayer. Other moieties that may be present in the antibodies or antibody fragments and are capable of self-assembling include thiol, disulphide and sulphide groups, which chemisorb spontaneously on metal surfaces through the sulphur-containing functional groups. If necessary and desired, new functional groups can also be introduced to the antibody or the antibody fragment by converting a structural part thereof to a functional group or by using linker molecules containing a functional group.

Alternatively, known methods for achieving controlled immobilisation of the antibodies can be used provided that specificity and sensitivity criteria are met. Such methods include, inter alia, selective binding trough protein A or protein G [see, for instance, Lekkala, J. and Sadowsky, J., Chemical Sensor Technology 5 (1994) 199-213], covalent attachment through free sulphydryl group in the hinge region of Fab' fragments [see, for instance, Fischer, B., et al., Langmuir 9 (1993) 136-140], and biotinylated antibodies coupled onto a surface by biotin/(strept)avidin chemistry [Morgan, H. and Taylor, D. M., Biosens. Bioelectron. 7 (1992) 405-410]. A direct attachment through a functional group present in the *H. pylori* antibodies or antibody fragments is preferred.

Similarly, the biomolecule-repellent molecules are also self-assembled through free sulphydryl or other sulphur-containing groups on the surface and cover the solid surface between the antibodies or the antibody fragments. The term "a biomolecule-repellent molecule" as used herein refers to molecules, which attach to the solid surface forming a hydrophilic layer between the immobilized antibodies and whose attraction forces are smaller than repulsion forces with respect to the analyte and contaminant (bio)molecules. The biomolecule-repellent molecules useful in the biosensor of the present invention include neutral, hydrophilic monomers or polymers, such as polyacrylamide, poly-N,N-dimethylacrylamide-, polyvinylalcohol, ethylene-vinyl-alcohol copolymer, poly(hydroxyethylmethacrylate), poly(ethyleneoxide) and poly(ethyleneglycol). Also other polymers, such polyethylenephalate, polytetrafluoroethylene, polyurethane and similar biocompatible polymers, can be used. Preferred biomolecule-repellent molecules useful in the present invention are polyacrylamide and poly-N,N-dimethylacrylamide, N-[tris(hydroxy-methyl)-methyl]acrylamide being especially preferred.

The biomolecule-repellent polymers are preferably attached to the solid surface covalently through a suitable functional group (terminal anchor group), such as sulfide, disulfide or thiol at one end of the polymer. Typically, the biomolecule-repellent polymers contain OH-groups at the other end of the molecules thus forming a hydrophilic layer. The thickness of the biomolecule-repellent molecule layer is preferably somewhat lower than the thickness of the antibody layer on the solid surface.

The solid surface of the carrier substrate useful in the present invention is of the type that can induce a change in a signal, which is emitted to the substrate to interact with the combination of substrate, immobilized antibodies or antibody fragments and bound analyte, and when subsequently detected, the signal change is indicative of an increase on the mass of the substance on the substrate (i.e. accumulation of the analyte molecules selectively bound to biomolecules immobilized on the surface of the substrate).

The solid surface material, which is used, depends on the chosen analysis method and is a film of a suitable thickness and suitable material, which can be used for the detection of increased mass on its surface. Thus, the solid surface can be a film of a surface plasmon resonance (SPR) compatible material, such as gold, silver, copper, aluminium, palladium, or other suitable metal, preferably gold, when a SPR-measurement is used for the analysis, an electrode covered with gold or other suitable metal, such as one of the above metals, preferably gold, when a quartz crystal microbalance (QCM) technique is used, or a suitable metal coating in a surface acoustic wave (SAW) device or on an electrode, when SAW-based techniques or electrochemical methods, respectively, are used.

Figure 2:
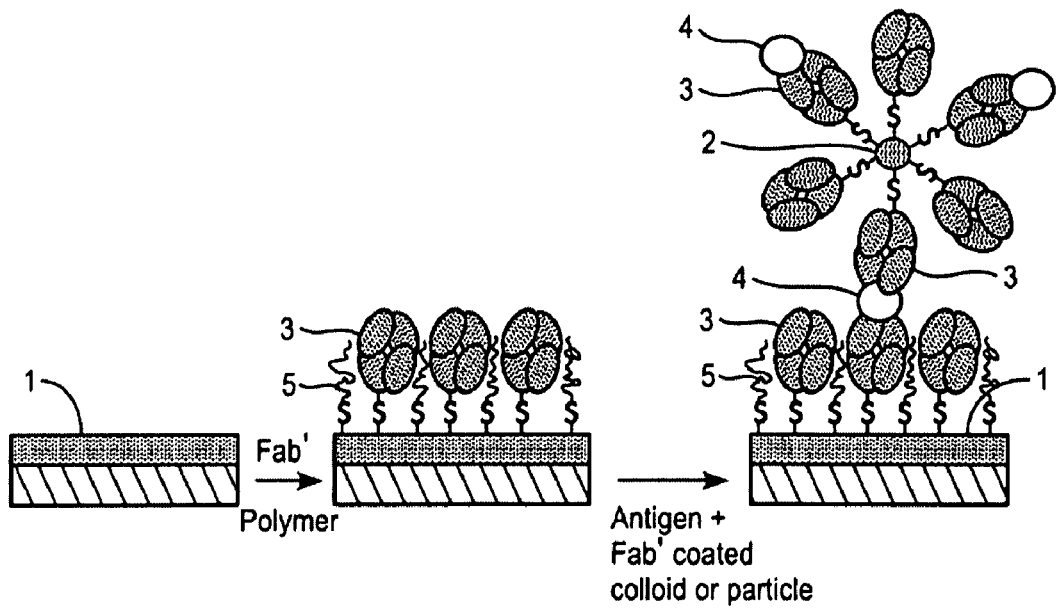
FIG. 2 is a schematic representation of a carrier substrate/biosensor used in the method of the present invention with colloids/nanoparticles (2) for the amplification of the detection/signal. All other designators (1 and 3-5) are the same as in FIG. 1 above.

Optionally, if desired, separate particles, such as colloids or nanoparticles, of the similarly coated material as used in the solid surface can be included to the reaction mixture to amplify the detection signal (FIG. 2).

The antibodies and antibody fragments useful in the present invention can be any polyclonal or monoclonal antibodies or antibody fragments that are able to bind a *H. pylori* antigen. Mixtures of antibodies or antibody fragments raised against different *H. pylori* strains can also be attached to the carrier substrate to ascertain the detection sensitivity and specificity. Preferably monospecific polyclonal or monoclonal antibodies, most preferably monoclonal antibodies, or antigen-binding fragments thereof are used. To ensure the correct orientation, antibody fragments, i.e. (Fab')$_2$ and Fab' fragments, are preferred, the Fab' fragments being most preferred due to increased sensitivity. Illustrative examples are commercial monoclonal anti-*H. pylori* antibodies produced by clones 7101 and 7102 available from Medix Biochemica, Kauniainen, Finland, or antigen-binding fragments thereof.

Preferably, antibodies or antibody fragments belonging to IgG class are attached to the carrier substrate. However, where applicable, antibodies or antibody fragments belonging to IgM or IgA immunoglobulin classes can also be used.

The amounts of the antibodies or the antibody fragments used for the preparation of the carrier substrate as well as the preparation of the antibody fragments, where necessary, are within the knowledge of a person skilled in the art. Similarly, the amount of the biomolecule-repellent molecules used for the preparation of the carrier substrate can be determined using standard procedure by a person skilled in the art. Usually both the antibodies or antigen-binding fragments thereof and the biomolecule-repellent molecules are used in excess to ensure the optimal performance of the carrier substrate. In this respect, a reference is made to Example 1 set forth below and also to Finnish Application 20011877 incorporated herein by reference. In the preparation of the carrier substrate the antibody or the antibody fragment and the biomolecule-repellent molecules can be attached at the same time or sequentially. Alternatively, the biomolecule-repellent molecules can be attached to a carrier substrate already containing the immobilized antibodies.

The layer containing the antibody or the antibody fragment can be regenerated with a suitable solution, such as a 0.1 M HCl-glycine solution, pH 1-2, or 0.1 M phosphate buffer, pH 2-7. This affords an additional advantage to the carrier substrate, i.e., the substrate can be reused up to 10 times, which provides substantial advantages in both cost and convenience to the user.

The biological sample to be analysed can be any liquid or soluble biological sample. Thus the biological sample can be whole blood, serum, urine, saliva or other mucous secretion, lacrimal fluid or faeces. Also samples derived from a biopsy sample can be analysed with the methods of the present invention, if desired. The sample can be analysed as such or as concentrated using conventional techniques.

The correct orientation of the specific antibodies or antibody fragments and the use of biomolecule-repellent molecules in the carrier substrate of the present invention afford a simple and rapid non-invasive detection of *H. pylori* infection from biological samples. Additionally, these features afford specificity and sensitivity high enough to perform, if desired, a quantitative or a semi-quantitative measurement of the *H. pylori* antigens in addition to a qualitative measurement. This is of advantage particularly in the follow-up of the efficacy of the pharmacotherapy of *H. pylori* infection, whereby the usually quite heavy and long treatment protocol can be changed at an early stage, if the chosen treatment is not effective. The total cure can be demonstrated much earlier than with an antibody measurement. Also new or recurrent infections can be easily detected. The quantitative measurement of *H. pylori* antigens may also provide information on the duration and severity of the infection, which may be helpful in the choice of the medication.

In the method of the invention a biological sample obtained from a patient suffering from or suspected of suffering from *H. pylori* infection is contacted with a carrier substrate, described in detail above, of biosensor and detecting the signal resulting from the formation of an antibody-antigen-complex. The carrier substrate and the biosensor of the invention are applicable to any standard platforms employing biosensor-based measurements. However, the detection methods that are particularly suitable in the method of the present invention are surface plasmon resonance (SPR), thickness shear mode resonator technique, such as quartz crystal microbalance (QXM), surface acoustic waves (SAW devices) and electrochemical measurements. Sulface plasmon resonance (SPR) is specially preferred.

The test kit of the present invention contains reagents for performing the method of the present invention. Specifically, the test kit contains a biosensor comprising a carrier substrate onto which specific antibodies against *H. pylori* or antigen-binding fragments thereof have been directly attached together with biomolecule-repellent molecules, which cover the surface between the immobilized antibodies or the antibody fragments, and the reagents needed for the measurement, such as standards, controls, washing solutions and dilution solutions.

The present invention is elucidated with the following non-limiting examples.

EXAMPLE 1

A General Procedure for the Preparation of the Carrier Substrate of the Invention For the preparation of the carrier substrate, Fab'-fragments were first prepared from a specific monoclonal anti-*H. pylori* antibody as follows. First, F(ab')$_2$ fragments were prepared with ImmunoPure F(ab')$_2$ Preparation Kit (PIERCE, USA) from monoclonal anti-*H. pylori* antibodies, such as monoclonal anti-*H. pylori* antibodies clones 7101 and 7102 (Medix Biotechnica, Kauniainen, Finland). Other known commercial kits and methods can equally be used. Then the F(ab')$_2$ fragments were split into Fab' fragments with dithiothreitol (DTT, Merck) in a HEPES/EDTA buffer containing 150 mM NaCl, 10 mM HEPES, 5 mM EDTA, pH 6.0, typically over night in a microdialysis tube as described by Ishikawa [Ishikawa, E., J. Immunoassay 4 (1983) 209-320]. Briefly, F(ab') 2 fragments at a concentration of 0.2-0.5 mg/ml were mixed with HEPES/EDTA buffer and 6.25 mM DTT solution in a microdialysis tube. The dialysis tube was immersed in 250 ml of argon-purged HEPES/EDTA buffer and dialysed over night at room temperature under argon. The Fab' fragments were maintained under argon and used immediately for attachment.

The solid surface was prepared as follows. Glass slides were first coated with a thin film of titanium to increase the adhesion of gold and then with a thin film of gold by vacuum evaporation. Immediately before use the slides were cleaned in a hot solution of $H_2O_2NH_4OH:H_2O$ (1:1:5) and rinsed with water. The slides were attached via an index matching oil to a SPR prism on a Surface Plasmon Resonance Device (SPRDEVI, VTT, Tampere, Finland), the flow cell was assembled on the prism and the flow cell was thoroughly rinsed with a buffer solution containing 10 mM HEPES, 150 mM NaCl, pH 6, prepared in high purity water (18.2 MΩcm; Milli-Q system, Millipore Co., Bedford, USA).

The Fab' fragments (850 μl) at a concentration of 70 μg/ml in 10 mM HEPES/EDTA buffer, pH 6, were added into the flow cell. The Fab' fragments were allowed to interact with the gold-coated surface typically for 5 minutes, followed by rinsing the surface with the HEPES/EDTA buffer for 5 minutes. Then the buffer was changed to 0.1 M phosphate-buffered saline (PBS), pH 7.2, and 1-1.5 ml of a of N-[tris(hydroxy-methyl)methyl]-acrylamide solution at a concentration of 0.15 mg/ml in the PBS buffer were allowed to interact with the surface for 5 minutes. The surface was then blocked with bovine serum albumin (BSA).

EXAMPLE 2

A General Procedure for the Measurement of *H. pylori* Antigens with SPR

*H. pylori* antigens can be measured in a biological sample with the following general SPR procedure. The surface of carrier substrate prepared as described in Example 1 is rinsed with PBS, pH 7.2. A negative sample (blank) is run at first. The negative sample used depends on the biological sample to be measured. Thus when, for example, a stool sample is to measured, the negative sample is a stool sample negative for *H. pylori*, when a urine sample is to be measured, the negative sample is a urine sample obtained from a subject without *H. pylori* infection, and when a serum sample is to be measured, the negative sample is a serum sample obtained from a subject without *H. pylori* infection. Then surface of the carrier substrate is sequentially brought into contact with the standard solutions, positive and negative controls and the samples by filling the flow cell of the measuring device for 10 minutes each with the solution to be measured and recording the SPR signal. The flow cell is rinsed with PBS, pH 7.2, for 5 minutes between measurements.

EXAMPLE 3

Preparation of a Standard Curve and the Reproducibility of the Measurement

The *H. pylori* antigen, which was used as a standard, was extracted from the bacterial mass of *H. pylori* strain ATCC 49503 using the glycine-acid extraction procedure described by Rautelin and Kosunen [J. Clin. Microbiol. 25 (10) (1987) 1944-1951]. The protein concentration was determined with Bradford assay [Bradford, Anal. Biochem. 72 (1976) 248]. The standards were diluted in 0.1 M PBS, pH 7.2, to concentrations of 0.001, 0.01, 0.1, 1, 10, 100 and 270 μg/ml and run following the general procedure described in Example 2. Three separate measurements were made on consequent days to analyse the reproducibility.

Figure 3:
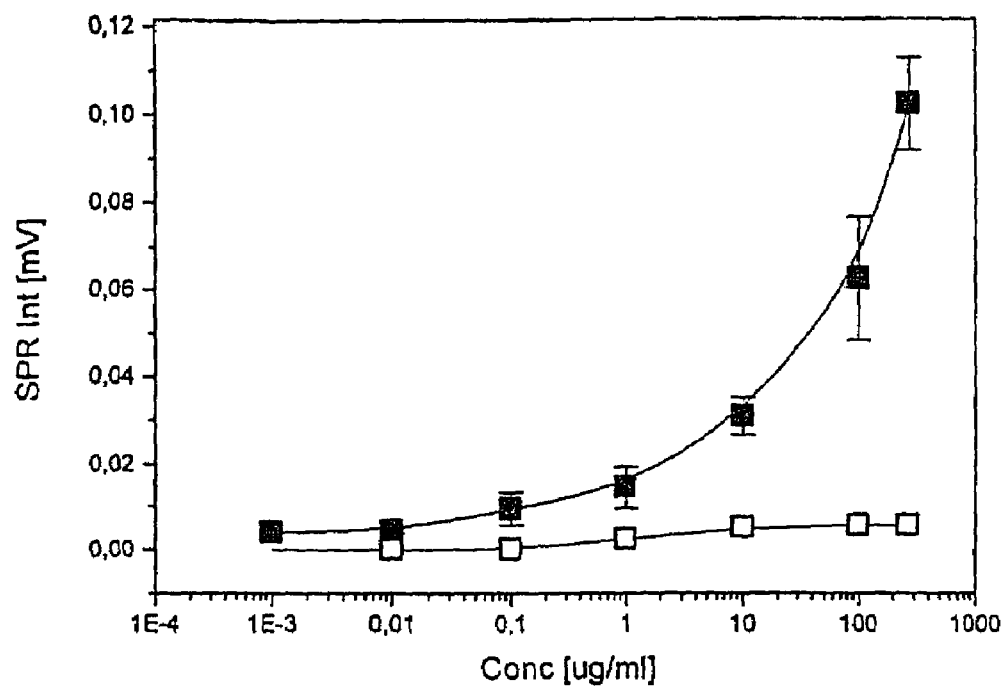
FIG. 3A shows a standard curve for *H. pylori* antigen binding using SPR measurement. The horizontal axis represents the antigen concentration. The vertical axis represents the SPR measurement. The curve with closed black squares represents the *H. pylori* antigen dilution. The curve with open squares represents a control sample.
FIG. 3B shows an SPR standard curve demonstrating the reproducibility of the measurement. *H. pylori* antigen dilutions were measured in three separate runs made on consecutive days. The different symbols represent the same antigen preparation measured in different runs.
Figure 3:
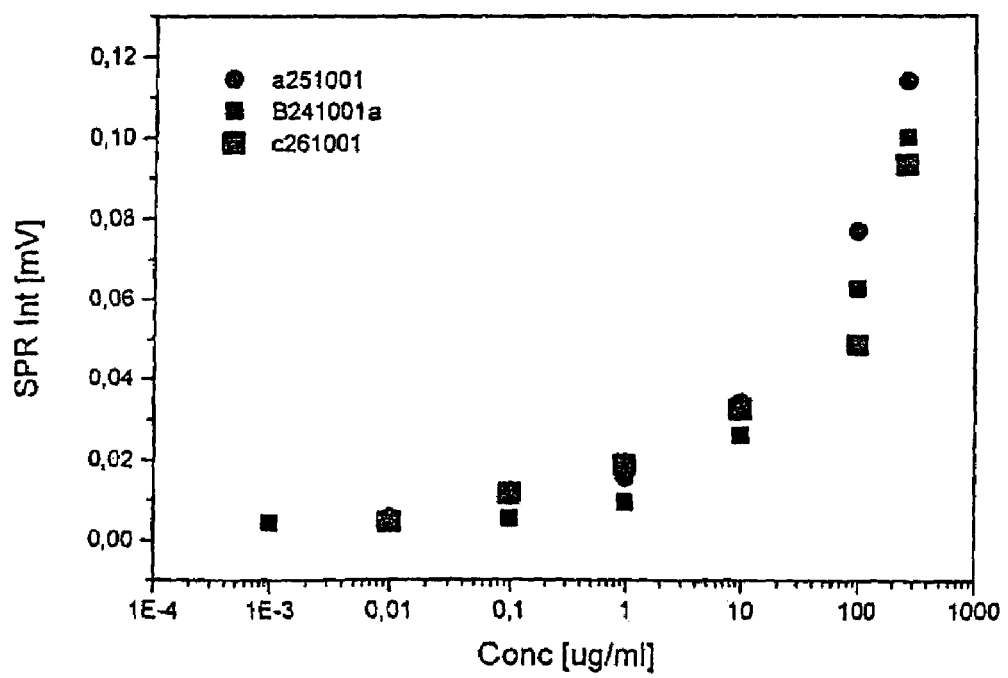

The results are shown in FIG. 3A. The standard curve shown in FIG. 3A shows that the response is directly comparable with the antigen concentration on a semilogarithmic scale. Table 1 shows the standard deviations from three separate measurements of the standard curve on consequent days (FIG. 3B). Excellent reproducibility is obtained.

TABLE 1

SPR intensity obtained with the standards

| H. pylori concentration [µg/ml] | Intensity change [mV] | SD [mV] |
| --- | --- | --- |
| 0.001 | 0.004 | |
| 0.01 | 0.005 | 0.001 |
| 0.1 | 0.009 | 0.004 |
| 1 | 0.014 | 0.005 |
| 10 | 0.031 | 0.004 |
| 100 | 0.062 | 0.014 |
| 270 | 0.102 | 0.010 |

EXAMPLE 4

Detection of H. pylori Antigen in Urine and Stool Samples

Urine and stool samples obtained from patients with H. pylori infection (the infection verified by biopsy) and from a non-infected patient were analysed with the SPR according to the general procedure described in Example 2. H. pylori infection of the patients had been diagnosed from a biopsy sample with a commercial rapid urease test and confirmed by an evaluation of a pathologist.

Stool samples were prepared as follows. 0.1 g of stool were suspended in 500 µl of 0.1 M phosphate buffered saline, pH 7.2, and vortexed for 15 seconds. The suspension was centrifuged for 5 minutes at 5000 rpm and the supernatant was used in the measurement. Urine samples were analysed as such.

Two of the stool samples measured, samples BSF37 and BSF48, were from patients with H. pylori infection verified by biopsy. The third sample, BSF51 was from a patient negative for H. pylori. The measurements were performed with two separate films. The results are shown in FIG. 4. The non-specific binding to the layer was 0.0013±0.0006 mV (n=3, two different layers were compared). The response of patient sample BSF48 was 0.0136±0.0004 mV and of patient sample BSU37 0.0113 mV, i.e. tenfold and eight-fold, respectively, to that of the background. The negative patient sample BSF51 gave an intensity of 0.00096 mV. The results clearly show that the method of the invention specifically detects the H. pylori antigen present in stool samples.

Two of the urine samples measured, samples 1 and 3, were from patients with H. pylori infection verified by biopsy. The third sample, sample 2, was from a patient negative for H. pylori. The results are shown in FIG. 5. The non-specific binding to the layer was 0.0185±0.0050 mV. The response of patient sample 1 was 0.117 mV and of patient sample 3 0.044 mV, i.e. 6.3-fold and 2.4-fold, respectively, to that of the background. The negative patient sample 2 gave an intensity of 0.008 mV. The results clearly show that the method of the invention specifically detects the H. pylori antigen present in urine samples.

The invention claimed is:

1. A non-invasive method for the detection of the presence or absence of a *Helicobacter pylori* antigen in a biological sample comprising:

a) contacting a biological sample obtained from a patient suffering or suspected of suffering from H. pylori infection with a biosensor comprising (i) a carrier substrate which has a solid surface, (ii) antibodies against H. pylori, or antigen-binding fragments-thereof, and (iii) hydrophilic biomolecule-repellent molecules; wherein:
the solid surface of the carrier substrate produces a surface plasmon resonance (SPR) signal;
both the antibodies or antigen-binding fragments thereof and the hydrophilic biomolecule-repellent molecules comprise a functional group having affinity for the solid surface of the carrier substrate;
both the antibodies or antigen-binding fragments thereof and the hydrophilic biomolecule-repellent molecules are covalently attached directly to the solid surface of the carrier substrate through the functional group having affinity for the solid surface of the carrier substrate, thereby forming a monolayer;
both the antibodies or antigen-binding fragments thereof and the hydrophilic biomolecule-repellent molecules are self-assembled on the solid surface of the carrier substrate; and
the antibodies or antigen binding fragments thereof are attached to the solid surface of the carrier substrate at the same time as, or prior to, attachment of the hydrophilic biomolecule-repellent molecules to the solid surface of the carrier substrate; and b) detecting the signal resulting from the formation of an antibody-antigen-complex;
wherein the hydrophilic biomolecule-repellent molecules are neutral hydrophilic monomers or polymers selected from the group consisting of polyacrylamide, poly-N,N-dimethylacrylamide, and N-[tris(hydroxymethyl)methyl]acrylamide.

2. The method of claim 1, wherein the functional group having affinity for the solid surface of the carrier substrate is a sulfur-containing functional group.

3. The method of claim 2, wherein the sulfur-containing functional group comprises at least one of a thiol group, a disulfide group, or a sulfide group.

4. The method of claim 1, wherein the solid surface of the carrier substrate is a film of a surface plasmon resonance (SPR) compatible material.

5. The method of claim 1, wherein the solid surface of the carrier substrate is a film of a metal.

6. The method of claim 5, wherein the metal is gold, silver, copper, aluminum, or palladium.

7. The method of claim 6, wherein the metal is gold.

8. The method of claim 1, wherein:
the functional group having affinity for the solid surface of the carrier substrate comprises at least one of a thiol group, a disulfide group, or a sulfide group;
the solid surface of the carrier substrate is gold, silver, copper, aluminum, or palladium; and
both the antibodies or antigen-binding fragments thereof and the hydrophilic biomolecule-repellent molecules are attached directly to the solid surface of the carrier substrate through covalent bonds between the gold, silver, copper, aluminum, or palladium atoms of the solid surface of the carrier substrate and the sulfur atoms of the functional group having affinity for the solid surface of the carrier substrate.

9. The method of claim 1, wherein the biomolecule-repellent molecules are polyacrylamide.

10. The method of claim 1, wherein the biomolecule-repellent molecules are poly-N,N-dimethylacrylamide.

11. The method of claim 1, wherein the biomolecule-repellent molecules are N-[tris(hydroxymethyl)methyl]acrylamide.

12. A test kit for the detection of the presence or absence of a *H. pylori* antigen in a biological sample, the test kit comprising:

a) a biosensor comprising: (i) a carrier substrate which has a solid surface, (ii) antibodies against *H. pylori* or antigen-binding fragments thereof, and (iii) hydrophilic biomolecule-repellent molecules; wherein:

the solid surface of the carrier substrate produces a surface plasmon resonance (SPR) signal;

both the antibodies or antigen-binding fragments thereof and the hydrophilic biomolecule-repellent molecules comprise a functional group having affinity for the solid surface of the carrier substrate;

both the antibodies or antigen-binding fragments thereof and the hydrophilic biomolecule-repellent molecules are covalently attached directly to the solid surface of the carrier substrate through the functional group having affinity for the solid surface of the carrier substrate, thereby forming a monolayer; and both the antibodies or antigen-binding fragments thereof and the hydrophilic biomolecule-repellent molecules are self-assembled on the solid surface of the carrier substrate; and the antibodies or antigen binding fragments thereof are attached to the solid surface of the carrier substrate at the same time as, or prior to, attachment of the hydrophilic biomolecule-repellent molecules to the solid surface of the carrier substrate, and b) reagents needed for the calibration and quality control of the detection; and c) auxiliary reagents;

wherein the hydrophilic biomolecule-repellent molecules are neutral hydrophilic monomers or polymers selected from the group consisting of polyacrylamide, poly-N,N-dimethylacrylamide, and N-[tris(hydroxymethyl)methyl] acrylamide molecules.

13. The test kit of claim 12, wherein the auxiliary reagents are wash solutions or dilution buffers.

14. The test kit of claim 12, wherein the biomolecule-repellent molecules are polyacrylamide.

15. The test kit of claim 12, wherein the biomolecule-repellent molecules are poly-N,N-dimethylacrylamide.

16. The test kit of claim 12, wherein the biomolecule-repellent molecules are N-[tris(hydroxymethyl)methyl]acrylamide.

* * * * *